US009808446B2

(12) United States Patent
Megiddo et al.

(10) Patent No.: US 9,808,446 B2
(45) Date of Patent: *Nov. 7, 2017

(54) METHOD FOR DECREASING SYMPTOMS OF ALCOHOL CONSUMPTION

(71) Applicant: Alcobra Ltd., Tel Aviv (IL)

(72) Inventors: Gur Megiddo, M.P. Judean Hills (IL); Dalia Megiddo, M.P. Judean Hills (IL); Rina Yamin, Ganne Yohannan (IL); Yaron Ilan, Jerusalem (IL); Shimon Amselem, Rehovot (IL)

(73) Assignee: Alcobra Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/678,502

(22) Filed: Apr. 3, 2015

(65) Prior Publication Data

US 2015/0209338 A1 Jul. 30, 2015

Related U.S. Application Data

(63) Continuation of application No. 12/667,272, filed as application No. PCT/IL2008/000917 on Jul. 3, 2008, now abandoned.

(30) Foreign Application Priority Data

Jul. 3, 2007 (IL) .......................... 184389
Nov. 5, 2007 (IL) .......................... 187159

(51) Int. Cl.
| | |
|---|---|
| *A61K 31/401* | (2006.01) |
| *A61K 31/44* | (2006.01) |
| *A61K 31/4015* | (2006.01) |
| *A61K 31/4415* | (2006.01) |
| *A61K 31/455* | (2006.01) |
| *A61K 9/20* | (2006.01) |
| *A61K 9/46* | (2006.01) |
| *A61K 9/00* | (2006.01) |
| *A61K 9/16* | (2006.01) |
| *A61K 9/50* | (2006.01) |
| *A61K 9/70* | (2006.01) |
| *A61K 47/32* | (2006.01) |
| *A61K 47/38* | (2006.01) |

(52) U.S. Cl.
CPC ............ *A61K 31/44* (2013.01); *A61K 9/0007* (2013.01); *A61K 9/0095* (2013.01); *A61K 9/1635* (2013.01); *A61K 9/1652* (2013.01); *A61K 9/2054* (2013.01); *A61K 9/5026* (2013.01); *A61K 9/7061* (2013.01); *A61K 31/4015* (2013.01); *A61K 31/4415* (2013.01); *A61K 31/455* (2013.01); *A61K 47/32* (2013.01); *A61K 47/38* (2013.01)

(58) Field of Classification Search
CPC ............ A61K 31/4415; A61K 31/4015; A61K 9/0053
See application file for complete search history.

(56) References Cited

U.S. PATENT DOCUMENTS

| | | | |
|---|---|---|---|
| 4,313,952 | A | 2/1982 | Bandacci |
| 5,594,030 | A | 1/1997 | Conte et al. |
| 5,714,531 | A | 2/1998 | Fujimura et al. |
| 5,942,530 | A | 8/1999 | Panetta et al. |
| 6,126,969 | A | 10/2000 | Shah et al. |
| 6,541,043 | B2 | 4/2003 | Lang |
| 8,476,304 | B2 | 7/2013 | Megiddo et al. |
| 8,710,067 | B2 | 4/2014 | Yamin et al. |
| 2002/0119195 | A1 | 8/2002 | Sen et al. |
| 2002/0192303 | A1 | 12/2002 | Arver et al. |
| 2003/0147957 | A1 | 8/2003 | Licht et al. |
| 2003/0148992 | A1 | 8/2003 | Block et al. |
| 2004/0162270 | A1 | 8/2004 | Oslick et al. |
| 2005/0271739 | A1 | 12/2005 | Wang |
| 2007/0248696 | A1 | 10/2007 | Maletto et al. |
| 2008/0146577 | A1 | 6/2008 | Matalon et al. |
| 2008/0226719 | A1 | 9/2008 | Roses et al. |
| 2009/0081179 | A1 | 3/2009 | Kiliaan et al. |
| 2012/0264781 | A1 | 10/2012 | Yamin et al. |
| 2012/0277270 | A1 | 11/2012 | Megiddo et al. |
| 2013/0012549 | A1 | 1/2013 | Yamin et al. |

FOREIGN PATENT DOCUMENTS

| | | |
|---|---|---|
| CN | 1490006 A | 4/2004 |
| CN | 1650862 | 8/2005 |
| EP | 511943 A2 | 11/1992 |
| EP | 0655240 | 5/1995 |
| FR | 2172906 A1 | 10/1973 |
| GB | 1286161 A | 8/1972 |
| JP | 2138128 | 5/1990 |
| JP | 2006022056 | 1/2006 |

(Continued)

OTHER PUBLICATIONS

Manor et al., J. Clin. Psychiatry 73, 1517-23 (2012).*
Zou, Lijia, Pharmacy, China Medicine Science and Technology Press, Dec. 31, 1996, pp. 500-506 (partial English translation).
Caballeria et al., "Metadoxine accelerates fatty liver recovery in alcoholic patients: results of a randomized double-blind, placebo-control trial," J. Hepatol. 28, 54-60 (1998).
Cannon "Chapter Nineteen," in Burger's Medicinal Chemistry and Drug Discovery, Fifth Edition, vol. 1: Principles and Practice, Wiley-Interscience, New York, 1995, pp. 783-802.
Pramming et al., "Cognitive function during hypoglycaemia in type I diabetes mellitus," British Medical Journal, 292:647-650 (1986).
Sheridan, "The Most Common Chemical Replacements in Drug-Like Compounds," J. Chem. Inf. Comput. Sci., 42:1 03-1 08 (2002).

(Continued)

*Primary Examiner* — Theodore R West
(74) *Attorney, Agent, or Firm* — Cooley LLP; Ivor R. Elrifi; Cynthia Kozakiewicz

(57) ABSTRACT

The present invention relates to methods and compositions of metadoxine and physiologically compatible active derivatives thereof, and their use for decreasing symptoms of alcohol consumption as well as in the prevention of alcohol consumption related symptoms in subjects in need thereof.

10 Claims, 4 Drawing Sheets

(56) References Cited

FOREIGN PATENT DOCUMENTS

| WO | WO 94/18965 A1 | 9/1994 |
|---|---|---|
| WO | WO 03/003981 A2 | 1/2003 |
| WO | WO 2005/048974 | 6/2005 |
| WO | WO 2008/066353 | 6/2008 |
| WO | WO 2010/013242 A1 | 2/2010 |
| WO | WO 2010/150261 A1 | 12/2010 |

OTHER PUBLICATIONS

University of Pennsylvania, "Fighting Sleep: Researchers Reverse Cognitive Impairment Caused by Sleep Deprivation," ScienceDaily, Oct. 27, 2009. pp. 1-2.
Azawu et al. "Physical Pharmacy," Latest Pharmaceutics, (2001):83-93. (Japanese original and partial English translation).
"Prolongation Substances (Prolongators)," Technology of Drug Forms, Moscow, Russia: Meditsina Publishers, Kondratieva, ed., vol. 1, Par. 5.3.4.(1991):1 06-108. (Russian Original and English Translation).
Biotics, (2002):18. (Russian Original and English Translation).
Calabrese et al. "Effects of Mexadoxine on Cellular Formation of Fatty Acid Ethyl Esters in Ethanol Treated Rats," Int. J. Reac. 17.3(1995):1 01-108.
Elia et al. "Treatment of Attention-Deficit-Hyperactivity Disorder," N. Engl. J. Med. 340.10(1999):780-788.
Gutierrez-Ruiz et al. "Metadoxine Prevents Damage Produced by Ethanol and Acetaldehyde in Hepatocyte and Hepatic Stellate Cells in Culture," Pharma. Res. 44.5(2001):431-436.
Lingetti et al. "Treatment of Cerebral Vasculopathies With Metadoxine," Acta Gerontal. 30.3(1980):230-234. (English Translation).
"Intestinal Permeation Enhancers" by Aungst, J. Pharm. Sci. 89, 429-42 (2000).
"Efficacy Study of Metadoxine SR Formulation in Attention Deficit Hyperactivity Disorder (ADHD) Subjects (NCT00995085)," Clinicaltrials.gov (Oct. 2009).
"Vitamin B6." A/veda Pharma, 2001, Web, Feb. 2, 2005. http://www.alvedapharma.com/PDF/PyridoxineEnglish.pdf.
Ajay et al. "Design, Development and in Vitro Evaluation of Metdoxine Microbeads: Ionic Gelation Method," Pharma, Res. 5.1 (2011):62-69.
Annoni et al. "Pyridoxol L,2-Pyrrolidon-5 Carboxylate Prevents Active Fibroplasia in CCl4-Treated Rats," Pharnn. Res. 25.1(1992):87-93.
Johansson et al. "Studies on the Metabolism of Labeled Pyridoxine in Man," Ann. J. Clin. Nutr. 18(1966):185-196.
Lalazar et al. "A Novel Slow Release Formulation of Metadoxine Improves Motor and Cognitive Function, Decreases Craving After Alcohol Ingestion in Healthy Volunteers: Results of a Phase I Clinical Trial," Hepatol. 50.4(2009):611A. (Abstract #650).
Lingetti et al. "Treatment of Cerebral Vasculopathies With Metadoxine," Acta Gerontol. 30.3(1980):230-234. (English Abstract Only).
Pal'tsev et al. "Non-Alcoholic Fatty Liver Disease: Age Peculiarities, Breakthrough in Pathogenic Therapy," Eksp. Klin. Gastroenterol. 8(2009):19-25. (English Abstract Only).
Safonova et al. "Metadoxil in the Treatment of Hepatotoxic Action of Cytostatics," Issues Oncol. 5(2005):599-600. (Russian Original and English Abstract).
Sinforiani et al. "Effects of Metadoxine (Metadoxil ®) on the Early Phase of Cognitive Recovery in Abstinent Alcoholics", Clin. Trial. J. 27.2(1990):103-111.
Vonghia et al. "Acute Alcohol Intoxication", Eur. J. Int. Med. 19.8(2008):561-567.
"Metadoxil' Drug Information," ABC J. Jul. 7, 1997. (Russian Original and English Translation).
"Alcohol Dependence" Guidance for Medicine: Diagnostics and Therapy, The Merck Manual, 2(1997): 15. (Russian Original and English Translation).
"Results" Drug Preparations by Medical Scientific Manufacture Complex Biotica, Moscow (2002):17, 19, 20, 22, 24. Russian Original and English Translation).
Christie,"Scotland's Drinking Laws Set for Reform to Stem Alcohol Problems." BMJ, 327.7413(2003):467.
Felicioli et al. "Effects of Pyridoxine-Pyrrolidon-Carboxylate on Hepatic and Cerebral ATP Levels in Ethanol Treated Rats," Int. J. Clin. Pharmacal. Ther. Toxicol. 18.6(1980):277-280.
Guerrini et al. "A Follow Up Study on the Efficacy of Metadoxine in the Treatment of Alcohol Dependence," Substance, Abuse Treatment, Prevention and Policy. 1 (2006):35.
Yifan et al. "Influence of Metadoxine on the Concentration of Ethanol in Blood of Rats With Acute Ethanol Intoxication," J. Health Toxicol. 17.2(2003). (English Translation of Summary).
Pellegrini-Giampietro et al. "Pyrrolidone Carboxylic Acid in Acute and Chronic Alcoholism," Recenti Progressi Medicina. 80.3(1989):160-164.
Addolorato et al., "Metadoxine in the treatment of acute and chronic alcoholism: a review", Int. J. Immunopath. Pharmacal. 16(3):207-214 (2003).
Antonelli et al., "Pyroglutamic acid administration modifies the electrocorticogram and increases the release of acetycholine and gaba from the guinea-pig cerebral cortex", Pharmacal. Res. Commun. 16(2):189-197 (1984).
Langer, "New methods of drug delivery", Science 249(4976):1527-1533 (1990).
Lu et al., "Pharmacokinetics of metadoxine for injection after repeated doses in healthy Volunteers", Chin. Med. J. 120(2):166-168 (2007).
Morse et al., "The definition of alcoholism", JAMA 268(8):1 012-1014 (1992).
Shpilenya et al., Metadoxine in acute alcohol intoxication: a double-blind, randomized, placebo-controlled study, Alcoholism: Clin. Exp. Res. 26(3):340-346 (2002) (abstract only).

* cited by examiner

METHOD FOR DECREASING SYMPTOMS OF ALCOHOL CONSUMPTION

This application is a continuation of U.S. patent application Ser. No. 12/667,272, filed Jun. 23, 2010, which is a national stage filing under 35 U.S.C. 371 of International Patent Application No. PCT/IL2008/000917, filed Jul. 3, 2008 and published under PCT Article 21(2) in English, which claims the benefit of Israeli Patent Application No. 184389, filed Jul. 3, 2007 and of Israeli Patent Application No. 187159, filed Nov. 5, 2007. The specification of each above-listed application is herein incorporated by reference in its entirety.

FIELD OF THE INVENTION

The present invention relates to methods and compositions of metadoxine and functional, physiologically compatible derivatives thereof, and their use in decreasing symptoms of alcohol consumption as well as in the prevention of alcohol consumption related symptoms in subjects in need thereof.

BACKGROUND OF THE INVENTION

Social drinking (the consumption of alcohol without becoming intoxicated) is a social norm in many cultures and has long been considered an acceptable practice which allows people to socialize more freely and easily together. Drinking is relaxing for many people, and drinking before and during parties, at bars or restaurants, with meals and with family and friends are all acts considered to be within the realm of social drinking, when alcohol consumption is maintained so that intoxication is not reached.

More excessive or serious forms of drinking, often chronic, may be potentially harmful to the drinker and to others affected by the drinker. For example, drinking with the intent to get drunk or intoxicated, drinking and driving while under the influence of alcohol, loss of psychomotor coordination and speech, blackouts, vomiting, alcohol poisoning and associated deaths are considered among the harmful symptoms and effects of drinking that falls outside the scope of social drinking. It would be desirable to avoid these and other effects or consequences of excessive alcohol consumption.

Alcohol abuse, moreover, is a common problem in the general population all over the world. Alcohol abuse and alcoholism are responsible for a wide variety of medical problems, which are considered part of the new-age epidemics, among them the most recognized being alcohol-induced liver disease, primary and secondary malnutrition, and neuron damage, often leading to death.

The pharmaco-therapeutic aspect of alcoholism includes the use of drugs, with different actions and objectives. Metadoxine is a pyridoxine-pyrrolidone carboxylate (also known as pyridoxol L,2-pyrrolidon-5 carboxylate or pyridoxine 5-oxo-2-pyrrolidon-carboxylate) with significant alcohol scavenging properties which has been used to treat acute alcohol intoxication, poisoning, and certain acute alcohol syndromes (reviewed in Addolorato et al., *Int. J. Immunopathol. Pharmacal.* (2003) 16:207-214). Long term data show that metadoxine is safe for use by humans.

Metadoxine is capable of accelerating the elimination of alcohol from the blood and tissues, helping restore the functional structure of the liver and relieve neuro-psychological disorders associated with chronic alcohol intoxication and associated syndromes. In animal studies, metadoxine increased plasma clearance and urinary excretion of ethanol, inhibited the increased production of fatty acid esters in the liver during chronic alcohol intake, reduced oxidative stress and prevented glutathione depletion in hepatic tissues (Antonelli et al., *Pharmacol. Res. Commun.* (1984) 16:189-197). In the brain, metadoxine increased the level of GABA and acetylcholine in the frontoparietal cortex of guinea pigs.

Metadoxine is an ion-pair between pyrrolidone carboxylate (PCA) and pyridoxine (vitamin B6) with the two compounds linked in a single product by salification. The pairing with PCA synergistically increases the pharmacological activity of pyridoxine (see, e.g., U.S. Pat. No. 4,313,952). Metadoxine is freely soluble in water and in gastric fluid. Oral absorption of the drug is fast with high bioavailability (60-80%). The half life of metadoxine in human serum is short (40-60 minutes) without appreciable differences between oral and intravenous administration (Addolorato et al., supra; Lu Yuan et al., *Chin. Med. J.* 2007 120(2) 160-168).

Metadoxine is marketed in several countries as a prescription drug in the form of 500 mg tablets and 300 mg injections. Tablets contain 500 mg of metadoxine, microcrystalline cellulose and magnesium stearate. Ampoules contain 300 mg of metadoxine, sodium metabisulfite, EDTA sodium, methyl-p-hydroxybenzoate and water.

Maximal levels of ethanol appear in the blood stream 30-60 minutes after drinking. Due to the fast absorption of ethanol, stomach wash is ineffective against ethanol overdose. Because ethanol is miscible in water, it will be targeted to water-rich tissues, such as the brain, where it will cause the familiar symptoms. An average drink increases blood ethanol level to about 20 mg/dl, which can typically be metabolized and cleared in about one hour. Up-regulation of alcohol-dehydrogenase (ADH) in heavy drinkers may increase the ethanol clearance to about 30 mg/dl per hour.

There is thus a need for methods and compositions that are capable of quickly reducing alcohol levels and providing quick restoration of sobriety following alcohol consumption in any type of drinking, or that reduce or prevent symptoms of alcohol consumption, particularly in subjects that have not reached intoxication levels or who do not exhibit symptoms of chronic alcoholic related syndromes. It would be desirable, for example, to have a treatment which could be administered during or shortly after social drinking of any amount of alcohol that would enable the drinker to quickly become sober enough to legally drive. There is also a need for better treatment and prevention of acute and chronic alcohol intoxications and related diseases, such as alcoholism.

SUMMARY OF THE INVENTION

The present invention solves one or more of the problems referred to above by providing various methods for reducing or preventing effects of alcohol consumption by administering a metadoxine composition. Metadoxine compositions formulated for sustained or controlled release, optionally also including an immediate release component, and methods for using such sustained or controlled release metadoxine formulations of the invention, are also provided.

Accordingly, in certain aspects, the invention provides a method for decreasing or preventing symptoms or effects of alcohol consumption in a subject in need thereof, preferably wherein the subject has not reached intoxication, comprising administering a composition comprising metadoxine.

In certain aspects, the invention provides a method for preventing alcohol intoxication in a subject in need thereof, comprising administering a composition comprising metadoxine.

In certain aspects, the invention provides a method for reducing or eliminating blood alcohol levels in a subject in need thereof, preferably wherein the subject has not reached intoxication, comprising administering a composition comprising metadoxine.

In certain other aspects, the invention provides a composition comprising metadoxine formulated for sustained release or controlled release. In some aspects, the invention provides a composition comprising metadoxine, wherein a portion of the metadoxine is formulated for sustained or controlled release and a portion of the metadoxine is formulated for immediate release.

Accordingly, in any of the various embodiments of the methods of the invention described above, the composition may comprise metadoxine formulated for immediate release, sustained release, controlled release, or a combination of any of the foregoing. In any of the various embodiments of the above described methods, the administration is non-chronic administration. Moreover, the metadoxine may consist of or comprise a physiologically compatible metadoxine derivative as described herein.

In certain other aspects, the invention provides a method for increasing the mean $t_{max}$ of metadoxine in the blood of a subject in need thereof comprising administering a metadoxine composition of the invention formulated for sustained release or controlled release, optionally including a portion of the metadoxine formulated for immediate release.

In certain aspects, the invention provides a use of any one of the compositions of the invention in the manufacture of a therapeutic composition useful for practicing each of the methods of the invention as described herein, e.g., for reducing or preventing symptoms or effects of alcohol consumption; for preventing alcohol intoxication; for reducing or eliminating blood alcohol levels in a subject, or for increasing the mean $t_{max}$ of metadoxine in the blood of a subject, among others.

In any of the various embodiments of metadoxine compositions described herein (e.g., metadoxine formulated for immediate release, sustained release, controlled release, or a combination of any of the foregoing), the metadoxine may consist of or comprise a physiologically compatible metadoxine derivative, as described herein. In certain embodiments, metadoxine compositions are formulated for non-chronic administration, and preferably for non-invasive administration.

The present invention also provides delivery devices and kits comprising a metadoxine composition of the invention, and methods for their use in the treatment or prevention of alcohol consumption related symptoms. Kits may optionally include means for measuring or monitoring blood alcohol concentration (BAC) levels before, during or after administration of a metadoxine composition.

DESCRIPTION OF THE INVENTION

Definitions

Figure 1:
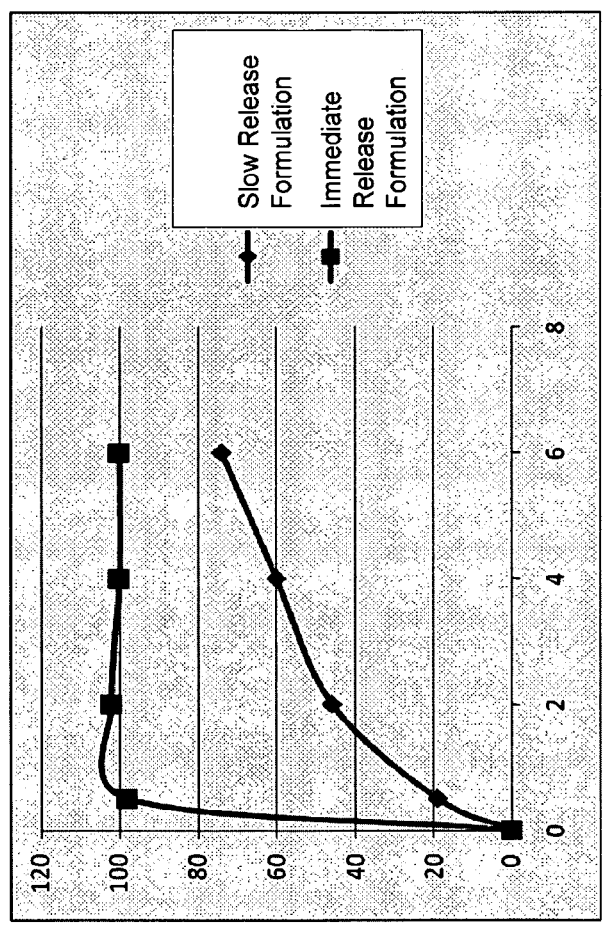
FIG. 1 shows a graph of the rate of release of certain metadoxine compositions of the present invention as described in Examples 2-3. The graph illustrates the difference between an immediate release formulation and a slow release formulation of metadoxine. Metadoxine (%) released vs. time (hours).

For convenience, certain terms employed in the specification, examples, and appended embodiments, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

The term "prophylactic" or "therapeutic" treatment refers to administration to a subject of one or more of the compositions of the invention. If it is administered prior to clinical manifestation of the unwanted condition (e.g., disease or other unwanted state of the host animal) then the treatment is prophylactic, i.e., it contributes to prevention of, i.e., protection of the subject against developing an unwanted condition, whereas if administered after manifestation of an unwanted condition, the treatment is therapeutic (i.e., it is intended to diminish, ameliorate or prevent progression of the unwanted condition or side effects therefrom).

The term "therapeutic effect" refers to a local or systemic effect in animals, particularly mammals, and more particularly humans, caused by a pharmacologically active substance or substances. The term thus means any substance intended for use in diagnosis, cure, mitigation, treatment or prevention of disease or in the enhancement of desirable physical or mental development and conditions in an animal or human. The term "therapeutically effective amount" means that amount of such a substance that produces some desired local or systemic effect at a reasonable benefit/risk ratio applicable to any treatment. In certain embodiments, a therapeutically-effective amount of a compound or composition will depend on its therapeutic index, solubility, and the like. For example, certain metadoxine formulations of the present invention may be administered in a sufficient amount to produce a reasonable benefit/risk ratio applicable to a selected treatment, as may be determined by the skilled artisan.

The term "effective amount" refers to the amount of a therapeutic reagent that when administered to a subject in an appropriate dose and regimen produces at least one desired result.

A "subject" or "patient" to be treated by a method of the invention may mean either a human or non-human animal, preferably a mammal.

Throughout this specification, the word "comprise" or variations such as "comprises" or "comprising" will be understood to imply the inclusion of a stated integer or groups of integers but not the exclusion of any other integer or group of integers.

The term "bioavailable" means that at least some amount of a particular compound is present in the systemic circulation. Formal calculations of oral bioavailability are described in terms of an F value ("Fundamentals of Clinical Pharmacokinetics," John G. Wegner, Drug Intelligence Publications; Hamilton, Ill. 1975). F values are derived from the ratio of the concentration of the parent drug in the systemic circulation (e.g., plasma) following intravenous administration to the concentration of the parent drug in the systemic circulation after administration by a non-intravenous route (e.g., oral). Therefore, oral bioavailability within the scope of the present invention contemplates the ratio or F value of the amount of parent drug detectable in the plasma after oral administration compared to intravenous administration.

The term "treating" or "treatment" refers to mitigating or alleviating at least on symptom of a condition, disease or disorder in a mammal, such as a human, or the improvement of an ascertainable measurement associated with a condition, disease or disorder.

The term "metadoxine" as used herein refers to the currently known and available form of metadoxine, which is an ion-pair between pyrrolidone carboxylate (PCA) and pyridoxine (vitamin B6) with the two compounds linked in a single product by salification. The term "metadoxine" as used herein is also intended to refer to and encompass any other active form of pyrrolidone carboxylate (PCA) in stable association with pyridoxine (vitamin B6). Stable association between the PCA and pyridoxine may be non-covalent, such as through a salt link, or other hydrostatic or electrostatic forces. Stable association, in other cases, may be accomplished by covalent bonding, e.g., by means of a linker or other chemical bond between the PCA and pyridoxine in which metadoxine activity is retained. The skilled artisan will be able to test the biological activity of any such complexes in standard metadoxine assays.

The term "acceptable derivative" with respect to metadoxine refers to any salt, conjugate, ester, complex or other chemical derivative of metadoxine or any of the moieties comprising the same, which, upon administration to a subject, is capable of providing (directly or indirectly) metadoxine or a metabolite or functional residue thereof, or measurable metadoxine activity. The term "physiologically compatible metadoxine derivative" may be used interchangeably herein with the term "acceptable derivative" and refers to a functional, active, pharmaceutically acceptable derivative of metadoxine.

The term "excipient" refers to an inactive substance used as a carrier for the active ingredient in a formulation.

The term "controlled release" refers to any formulation which delivers an agent at a controlled rate for an extended time and is designed to achieve a desired agent level profile.

The term "sustained release" is used in its conventional sense to refer to a formulation that provides for gradual release of an active material over an extended period of time, which in certain embodiments may also further result in substantially constant blood levels over an extended time period, i.e., controlled release.

The term "immediate release" is used in its conventional sense to refer to a formulation that provides for non delayed or controlled release of an active material upon administration.

The term "half-life" of a substance is the time it takes for a substance to lose half of its pharmacologic, physiologic, or other activity. Biological half-life is an important pharmacokinetic parameter and is usually denoted by the abbreviation $t_{1/2}$.

The term "non-invasive" refers to modes of treatment which do not puncture the skin.

The term "non-chronic administration" may be used interchangeably herein with the term "acute administration" and refers to giving a measured or non-measured quantity or portion of a medication to a subject on a non-regular basis. Non-chronic administration may be a single dose treatment or a multiple dose treatment, and may optionally be given over time. Typically but not always, a non-chronic administration is given to treat or prevent a non-chronic condition. Certain chronic conditions may also benefit from non-chronic administration of a metadoxine composition described herein.

The term "chronic administration" refers to giving a measured quantity of a medication on a regular basis to a subject. In some embodiments, chronic administration is to treat or prevent one or more chronic conditions or diseases. Chronic diseases have one or more of the following characteristics: they are permanent, leave residual disability, are caused by nonreversible pathological alteration, require special training of the patient for rehabilitation, or may be expected to require a long period of supervision, observation, or care.

The term "single dose treatment" refers to giving a measured quantity of a medication to be taken at one time. It is given to treat non-chronic conditions on an irregular basis, depending on personal need.

The term "alcoholism" refers to a primary chronic disease known as alcohol dependence syndrome, the most severe stage of a group of drinking problems. Alcoholism is considered a progressive disease, meaning that the symptoms and effects of drinking alcohol become increasingly more severe over time (Morse R. et al., *JAMA* 268(8):1012-4 (1992)).

The term "alcohol abuse" refers to repeated drinking despite alcohol-related physical, social, psychological, or occupational problems (The Diagnostic and Statistical Manual of Mental Disorders, IV). When alcohol abuse reaches the alcohol dependence stage, the person may also experience tolerance, withdrawal, and an uncontrolled drive to drink.

Art-recognized symptoms of alcohol consumption include: reduced activity in the central nervous system, loose muscle tone, loss of fine motor coordination, a staggering "drunken" gait, eyes appear "glossy," pupils may be slow to respond to stimulus, pupils may become constricted, decreased heart rate, lower blood pressure and respiration rate, decreased reflex responses, slower reaction times, skin may be cool to the touch (but the user may feel warm), profuse sweating, loss of fine motor coordination, or odor of alcohol on the breath. Symptoms of alcohol consumption and diagnostic criteria for alcohol intoxication include those described in the Diagnostic and Statistical Manual of Mental Disorders DSM-IV, e.g., section 303.00 Diagnostic Criteria for Alcohol Intoxication.

The term "alcohol intoxication" as used herein refers to a situation where the quantity of alcohol a person consumes exceeds the individual's tolerance for alcohol and produces, either during or shortly after drinking, clinically important psychological, behavioral or physical abnormalities, such as inappropriate aggression, and impaired judgment and social functioning. One or more of the following signs or symptoms of alcohol intoxication occur shortly after drinking: (1) slurred speech; (2) impaired motor coordination; (3) unsteady gait; (4) nystagmus (involuntary, irregular eye movement characterized by smooth pursuit of an object in one direction and saccadic movement in the other direction); (5) inattention and/or impaired memory; and (6) stupor or coma (see Diagnostic and Statistical Manual of Mental Disorders, Fourth Edition, (DSM-IV) 303.00).

Sobriety, intoxication, alcohol abuse, alcohol-related aggression or alcoholism may be measured according to one or more art recognized tests, such as psychomotor texts, serum alcohol level tests, for example accepted inhalation tests, Diagnostic and Statistical Manual of Mental Disorders, Fourth Edition, (DSM-IV), Alcohol Abstinence Self-Efficacy Scale (AASE; DiClemente, Carbonari, Montgomery, and Hughes, 1994), Barratt Impulsiveness Scale—11 (BIS-11; Barratt, 1994), State-Trait Anger Expression Inventory—2 (STAXI-2; Spielberger, 1999), Conflict Resolution, Impulsivity and Aggression Questionnaire (CRIAQ; Honess, Maguire, and Vanstone, 2001), Social Problem-Solving Inventory—Revised (SPSI-R; D'Zurilla, Nezu, and Maydeu-Olivares, 2002), Alcohol-Related Aggression Questionnaire (ARAQ; McMurran, Egan, Austin, and Charlesworth, under review), or The Alcohol Use Disorders Identification Test (AUDIT; Saunders, Aasland, Babor, et al., 1993). Levels of alcohol in the body may be measured in urine, blood, breath or saliva.

There is a wide range of variability in blood alcohol levels that different individuals can tolerate without becoming intoxicated. The range may be as great as from 0.3 to 1.5 mg/ml, although most states in the U.S. set the sobriety level for legally driving at 0.8 mg/ml (DSM-IV, 303.00; supra). Some users may develop significant behavioral changes or become intoxicated at a much lower Blood Alcohol Concentration (BAC) than the legal limit. This condition is known as "Alcohol Idiosyncratic Intoxication" or "Pathological Intoxication" (DSM-IV, 291.9) In general, however, the following symptoms are associated with increasing BAC levels:

0.02-0.03 BAC: No loss of coordination, slight euphoria and loss of shyness. Depressant effects are not apparent.

0.04-0.06 BAC: Feeling of well-being, relaxation, lower inhibitions, sensation of warmth. Euphoria. Some minor impairment of reasoning and memory, lowering of caution.

0.07-0.09 BAC: Slight impairment of balance, speech, vision, reaction time, and hearing. Euphoria. Judgment and self-control are reduced, and caution, reason and memory are impaired.

0.10-0.125 BAC: Significant impairment of motor coordination and loss of good judgment. Speech may be slurred; balance, vision, reaction time and hearing will be impaired. Euphoria. It is illegal to operate a motor vehicle at this level of intoxication.

0.13-0.15 BAC: Gross motor impairment and lack of physical control. Blurred vision and major loss of balance. Euphoria is reduced and dysphoria (anxiety, restlessness) is beginning to appear.

0.16-0.20 BAC: Dysphoria predominates, nausea may appear. The drinker has the appearance of a "sloppy drunk."

0.25 BAC: The drinker needs assistance in walking; total mental confusion. Dysphoria with nausea and some vomiting.

0.30 BAC: Loss of consciousness.

0.40 BAC and up: Onset of coma, possible death due to respiratory arrest.

The term "social drinking" refers to the consumption of alcohol in a safe, legal and socially acceptable manner usually without the intent of reaching the point of becoming intoxicated (i.e., to achieve alcohol intoxication). Although the amount of blood alcohol which leads to intoxication varies widely between individuals, three or fewer measured drinks (or a blood alcohol level of up to 0.05%) is generally considered to be within the social drinking range.

The term "session drinking" refers to drinking in large quantities over a single period of time, or session, without the intention of getting heavily intoxicated. The focus is on the social aspects of the occasion.

The term "binge drinking" refers to drinking alcohol solely for the purpose of intoxication, although it is quite common for binge drinking to apply to a social situation, creating some overlap in social and binge drinking. In certain embodiments, binge drinking refers to a woman consuming four drinks and a man consuming five drinks on a single drinking occasion. Because drinking occasions can last up to five or seven hours, many such bingers never become intoxicated.

The term "$t_{max}$" refers to the time to peak concentration. Calculation of time at which maximum concentration occurs after a single dose administration is performed according to the formula:

$$t_{max} = \frac{2.303}{\lambda_a - \lambda_z} \log \frac{\lambda_a}{\lambda_z}$$

where $\lambda_a$ and $\lambda_z$ are the apparent absorption and elimination rate constants, respectively.

Methods of Treatment and Prevention Using Metadoxine Compositions

In certain embodiments, the present invention provides a method for decreasing or preventing symptoms or effects of alcohol consumption in a subject in need thereof, especially wherein the subject has not reached intoxication, comprising administering a composition comprising metadoxine or a physiologically acceptable derivative thereof. In certain such embodiments, the method comprises non-chronic administration of a composition comprising metadoxine or a physiologically acceptable derivative thereof.

In certain embodiments, the present invention provides a method for preventing alcohol intoxication in a subject in need thereof, comprising administering a composition comprising metadoxine or a physiologically acceptable derivative thereof. In certain such embodiments, the method comprises non-chronic administration of a composition comprising metadoxine or a physiologically acceptable derivative thereof. In certain embodiments, methods for preventing intoxication include treatment of a subject with a composition comprising metadoxine or a physiologically acceptable derivative thereof, wherein the subject has previously reached intoxication and has subsequently sobered to a level that is below intoxication during a single drinking session.

In certain embodiments, the present invention provides a method for preventing alcoholism in a subject in need thereof, especially when the subject is not an acute alcoholic, comprising administering a composition comprising metadoxine or a physiologically acceptable derivative thereof.

In certain embodiments, the present invention provides a method for slowing the progression of alcoholism in a subject in need thereof, especially when the subject is not an acute alcoholic, comprising administering a composition comprising metadoxine or a physiologically acceptable derivative thereof.

In certain embodiments, the present invention provides a method for reducing or eliminating blood alcohol levels in a subject in need thereof, especially wherein the subject has not reached intoxication, comprising administering a composition comprising metadoxine or a physiologically acceptable derivative thereof. In certain such embodiments, the method comprises non-chronic administration of a composition comprising metadoxine or a physiologically acceptable derivative thereof.

In certain embodiments, the present invention provides a method for increasing the mean $t_{max}$ of metadoxine in the blood of a subject in need thereof comprising administering a composition comprising metadoxine or a physiologically acceptable derivative thereof, and especially wherein the composition comprises metadoxine or a physiologically acceptable derivative thereof formulated in whole or in part for sustained or controlled release. In certain such embodiments, the method comprises non-chronic administration of a composition comprising metadoxine or a physiologically acceptable derivative thereof formulated in whole or in part for sustained or controlled release. In certain embodiments of the invention, the mean $t_{max}$ of metadoxine in the blood of a subject is increased by 50%, 100%, 150%, 200%, 300%, 400% 500% or greater than 500%.

In certain embodiments, the application provides a method for increasing the half-life ($t_{1/2}$) of metadoxine in the blood or serum of a subject in need thereof comprising administering a composition comprising metadoxine or a physiologically acceptable derivative thereof, and especially wherein the composition comprises metadoxine or a physiologically acceptable derivative thereof formulated in whole or in part for sustained release or controlled release, optionally including a portion of the metadoxine formulated for immediate release. In certain embodiments of the invention, the $t_{1/2}$ of metadoxine in the blood or serum of a subject is increased by 50%, 100%, 150%, 200%, 300%, 400% 500% or greater than 500%.

In certain embodiments of the invention, metadoxine or a physiologically acceptable derivative thereof is used for immediate relief of drunkenness and regaining of sobriety in a subject in need thereof. In some embodiments, the subject has not reached alcohol intoxication levels. Such immediate relief has a great value in preventing various hazards, particularly motor vehicle accidents and other personal injuries. In certain such embodiments, the method comprises non-chronic administration of a composition comprising metadoxine or a physiologically acceptable derivative thereof, and may optionally be formulated in whole or in part for sustained or controlled release.

In certain embodiments, metadoxine or a physiologically acceptable derivative thereof is used for prolonged relief of drunkenness and regaining of sobriety in a subject in need thereof. In some embodiments, the subject has not reached alcohol intoxication levels. As above, such prolonged relief has a great value in preventing various hazards, particularly motor vehicle accidents and other personal injuries and also has a value in preventing and treating various symptoms and conditions associated with prolonged or frequent alcohol consumption. In certain such embodiments, the method comprises non-chronic administration of a composition comprising metadoxine or a physiologically acceptable derivative thereof, and may be optionally formulated in whole or in part for sustained or controlled release.

In certain embodiments, methods of the present invention may be used to treat a subject that has consumed alcohol but is not intoxicated. In certain embodiments, the methods of the invention may be used to treat a subject that has consumed alcohol but has not had an increase in psychomotor excitation and aggression. The methods of the present invention are intended for use in a variety of subjects before, during or after a variety of types of alcohol consumption of any amount. As each subject will present with different symptoms of alcohol consumption, blood alcohol concentrations alone are often useful but insufficient taken alone to describe subjects that will benefit from the compositions and methods of the present invention.

In certain embodiments, metadoxine compositions of the invention, e.g., formulated in whole or in part for sustained or controlled release, enable more efficient use of metadoxine in the treatment or prevention of non-chronic or chronic alcohol intoxications and syndromes and conditions related thereto.

In certain embodiments, the methods of the present invention may be used to prevent alcohol consumption related symptoms. In certain embodiments, subjects are treated before any alcohol consumption. In certain embodiments, subjects are treated after alcohol consumption, but before symptoms occur. In certain embodiments, subjects are treated after alcohol consumption, but before subjects are intoxicated. These embodiments are not mutually exclusive and may be combined in any desired combination.

In certain embodiments, the methods of the invention may prevent symptoms of alcohol consumption related to drinking one drink or a portion thereof. In certain embodiments, the methods of the invention may prevent symptoms of alcohol consumption related to drinking 2, 3, 4, 5 or more drinks.

In a yet further embodiment, the invention provides a method for the rapid or immediate restoration of sobriety following alcohol consumption in a subject in need of such treatment, comprising administering to said subject a composition comprising metadoxine or a physiologically acceptable derivative thereof. In certain embodiments, the subject has not reached alcohol intoxication levels. In certain embodiments, the administration is a non-chronic administration.

Furthermore, the invention provides a method of treatment and/or prevention of alcohol intoxication in a subject in need of such treatment, comprising administering to said subject a composition comprising metadoxine or a physiologically acceptable derivative thereof. In certain embodiments, the subject has not reached alcohol intoxication levels. In certain embodiments, the administration is a non-chronic administration.

Still further, the invention relates to a method of reducing alcohol blood, serum or tissue levels (e.g., muscle and other non-adipose tissues) in a subject in need of such treatment, comprising administering to said subject a composition comprising metadoxine or a physiologically acceptable derivative thereof. In certain embodiments, the subject has not reached alcohol intoxication levels. In certain embodiments, the administration is a non-chronic administration.

In certain embodiments, the invention provides a method of reducing or preventing an increase in BAC in a subject who is or has been consuming alcohol. In certain embodiments, the methods of the present invention may decrease or prevent an increase in BAC so that the subject has a BAC that is legally low enough to permit the subject to operate a motor vehicle. In certain embodiments, the compositions of the invention may prevent an increase in BAC beyond 1, 2, 3, or more levels as described in the definitions above. In certain embodiments, the compositions of the present invention may decrease BAC. In certain embodiments, the methods of the present invention may decrease BAC to a level where operating a motor vehicle is legally permitted. In certain embodiments, the compositions of the invention may decrease BAC by 1, 2, 3 or more levels as described in the definitions above.

In certain of the above described methods of the invention, the metadoxine or acceptable derivative thereof may be formulated for immediate release upon administration to the subject. In certain of the above described methods of the invention, the metadoxine or acceptable derivative thereof may be formulated for sustained and/or controlled release, and may optionally be formulated to have both immediate release and sustained and/or controlled release characteristics upon administration to the subject. In certain embodiments, metadoxine or a physiologically acceptable derivative thereof is formulated for non-chronic administration. Metadoxine formulations of the invention are described in more detail below.

Metadoxine Formulations and Administration Regimens

In certain embodiments, the present invention provides a composition comprising metadoxine or a physiologically acceptable derivative thereof formulated for sustained and/or controlled release when administered to a subject.

In certain embodiments, the present invention provides a composition comprising metadoxine or a physiologically acceptable derivative thereof wherein a portion of the metadoxine or derivative is formulated for sustained and/or controlled release and a portion of the metadoxine or derivative is formulated for immediate release when administered to a subject.

In certain embodiments, a metadoxine composition may decrease symptoms of alcohol consumption related to drinking one drink or a portion thereof. In certain embodiments, a metadoxine composition may decrease symptoms of alcohol consumption related to drinking 2, 3, 4, 5 or more drinks.

In certain embodiments, a metadoxine composition may be delivered in a single dose form, such as in a single dose drink. In certain embodiments, the compositions of the invention may be delivered in a single dose per drinking session. In certain embodiments, a metadoxine composition may be delivered in a single dose per binge drinking session. In certain embodiments, a metadoxine composition may be delivered in a single dose per acute alcohol related condition or potential condition. In certain embodiments, a metadoxine composition may be delivered in a single dose form per intoxication or potential intoxication. A potential condition or intoxication may be a state that would lead to the condition or intoxication without intervention. In certain embodiments, a single dose may be a partial dose, i.e., a portion of a single dosage form.

In certain embodiments, metadoxine compositions may be administered 24 hours, 12 hours, 8 hours, 4 hours, 2 hours, one hour, 55 minutes, 50 minutes, 45 minutes, 40 minutes, 35 minutes, 30 minutes, 25 minutes, 20 minutes, 15 minutes, 10 minutes, 5 minutes or immediately before alcohol consumption.

In certain embodiments, metadoxine compositions may be administered 24 hours, 12 hours, 8 hours, 4 hours, 2 hours, one hour, 55 minutes, 50 minutes, 45 minutes, 40 minutes, 35 minutes, 30 minutes, 25 minutes, 20 minutes, 15 minutes, 10 minutes, 5 minutes or immediately before alcohol related symptoms occur.

In certain embodiments, metadoxine compositions may be administered 24 hours, 12 hours, 8 hours, 4 hours, 2 hours, one hour, 55 minutes, 50 minutes, 45 minutes, 40 minutes, 35 minutes, 30 minutes, 25 minutes, 20 minutes, 15 minutes, 10 minutes, 5 minutes or immediately after alcohol consumption.

In certain embodiments, metadoxine compositions may be administered 24 hours, 12 hours, 8 hours, 4 hours, 2 hours, one hour, 55 minutes, 50 minutes, 45 minutes, 40 minutes, 35 minutes, 30 minutes, 25 minutes, 20 minutes, 15 minutes, 10 minutes, 5 minutes or immediately after alcohol related symptoms occur.

In certain embodiments, metadoxine compositions may be administered hourly, daily, weekly, monthly, yearly (e.g., in a time release form) or as a one-time delivery. The administration may be chronic or non-chronic. In certain embodiments, the delivery is not continuous. In certain embodiments, a metadoxine composition may be delivered in a single dose. In certain embodiments, the administration is once, twice, three times or more within a 12- to 24-hour period at which time the treatment is discontinued. In certain embodiments, the administration is once, twice, three times or more within a 24- to 48-hour period at which time the treatment is discontinued. In certain embodiments, the mode of delivery is non-invasive. In certain embodiments, the delivery is not intravenous.

In certain embodiment, the delivery may be continuous delivery for a period of time, e.g., intravenous delivery. In one embodiment of the methods described herein, the metadoxine composition is administered at least once per hour. In one embodiment of the methods described herein, the metadoxine composition is administered hourly. In one embodiment of the methods described herein, the metadoxine composition is administered at least once per day. In one embodiment, the metadoxine composition is administered daily. In one embodiment, the metadoxine composition is administered every other day. In one embodiment, the metadoxine composition is administered every 6 to 8 days, or more specifically, weekly.

In certain embodiments, effective serum levels of the active ingredient are achieved within from about 10 to about 20 or 30 or 40 or 50 or 60 minutes following metadoxine administration. In certain embodiments, effective serum levels of the active ingredient are achieved within from about 5 to about 20 or 30 or 40 or 50 or 60 minutes following metadoxine administration. In certain embodiments, effective serum levels of the active ingredient are achieved within from about 20 to about 20 or 30 or 40 or 50 or 60 minutes following metadoxine administration. In certain embodiments, effective serum levels of the active ingredient are achieved within about 5, 10, 15, 20, 30, 40, 50 or 60 minutes.

In certain embodiments, relief or decrease or prevention of alcohol related symptoms are achieved within from about 5 to about 20 or 30 or 40 or 50 or 60 minutes following metadoxine administration. In certain embodiments, relief or decrease or prevention of alcohol related symptoms are achieved within from about 10 to about 20 or 30 or 40 or 50 or 60 minutes following metadoxine administration. In certain embodiments, relief or decrease or prevention of alcohol related symptoms are achieved within from about 15 to about 20 or 30 or 40 or 50 or 60 minutes following metadoxine administration.

In certain embodiments, relief or decrease or prevention of alcohol related symptoms are achieved within from about one hour to about 2, 3, 4, 5, 6, 7 or 8 hours following metadoxine administration. In certain embodiments, relief or decrease or prevention of alcohol related symptoms are achieved within from about 2 hours to about 3, 4, 5, 6, 7 or 8 hours following metadoxine administration. In certain embodiments, relief or decrease or prevention of alcohol related symptoms are achieved within from about 3 hours to about 4, 5, 6, 7 or 8 hours following metadoxine administration. In certain embodiments, relief or decrease or prevention of alcohol related symptoms are achieved within from about 4 hours to about 5, 6, 7 or 8 hours following metadoxine administration. In certain embodiments, relief or decrease or prevention of alcohol related symptoms are achieved within from about 5 hours to about 6, 7 or 8 hours following metadoxine administration. In certain embodiments, relief or decrease or prevention of alcohol related symptoms are achieved within from about 6 hours to about 7 or 8 hours following metadoxine administration. In certain embodiments, relief or decrease or prevention of alcohol related symptoms are achieved within from about 7 to about 8 hours following metadoxine administration.

In certain embodiments, relief or decrease or prevention of alcohol related symptoms are achieved within about 5, 10, 15, 20, 30, 40, 50 or 60 minutes following metadoxine administration. In certain embodiments, relief or decrease or prevention of alcohol related symptoms are achieved within about 2, 3, 4, 5, 6, 7 or 8 hours following metadoxine administration.

In certain embodiments, the therapeutic effective amount, or dosage, may be dependent on the amount of alcohol consumed or to be consumed, state of intoxication, severity and responsiveness of the subject, or whether there is to be chronic or acute treatment. The course of metadoxine treatment may last from a few minutes to several days to several months, or until a cure is effected or a diminution of the symptom, condition or disease state is achieved. The treatment regimen selected may be chronic or non-chronic. Optimal dosing schedules may be calculated from measurements of drug accumulation in the body of the patient. Persons of ordinary skill can easily determine optimum dosages, dosing methodologies and repetition rates. In general, dosage is calculated according to body weight, and may be given once or more daily, weekly, monthly or yearly, or even once every 2 to 20 years. Persons of ordinary skill in the art can easily estimate repetition rates for dosing based on measured residence times and concentrations of the combined composition of the invention in bodily fluids or tissues. Following successful treatment, it may be desirable to have the patient undergo maintenance therapy to prevent the recurrence of the disease state, wherein the combined composition of the invention is administered in maintenance doses, once or more daily.

The present inventors have developed innovative approaches for the administration of metadoxine based on enteral (via the digestive tract) and/or parenteral (other routes than digestive tract) routes. These approaches provide for a rational design of delivery systems with desired properties based on the meticulous selection of the carrier, e.g. appropriate surfactants/co-surfactants composition or micro/nano particles (such as liposomes or nano-liposomes) entrapping the active ingredients, or other additives or excipients, for the delivery system of interest.

The enteral delivery systems may be designed for oral administration (tablets, sachets, lozenges, capsules, gelcaps, drops, or other palatable form) or rectal administration (suppository or (mini) enema form).

In addition, the delivery system of interest may be in liquid form, for example a drop solution, syrup. Furthermore, the delivery system of interest may be in form of a beverage or food article. Thus, the active ingredient/s used by the invention may be comprised in a beverage, particularly soft drinks like juices, nectars, water, sparkling water and other sparkling drinks, shakes, milk shakes and other milk-based drinks, and the like. Liquid preparations may also be in the form of concentrated syrups, for diluting with water or sparkling water. Alternatively, the active ingredient/s may be comprised in food articles, such as snack bars, health bars, biscuits, cookies, sweets, confectionery products, ice creams, ice lollies, and the like.

Still further, the invention relates to a food or beverage article comprising a physiologically active pyridoxine derivative, particularly pyridoxol L,2-pyrrolidon-5 carboxylate (metadoxine), for fast restoration of sobriety following alcohol consumption in a subject in need thereof, especially wherein the subject has not reached intoxication. In certain embodiments, consumption of the food or beverage article of the invention may lead to achievement of serum levels of the active ingredient within from about 10 to about 40-60 minutes following consumption thereof.

The parenteral ways include subcutaneous, transdermal (diffusion through the intact skin), transmucosal (diffusion through a mucous membrane), sublingual, buccal (absorbed through cheek near gumline) administration, or administration by inhalation. In certain embodiments, the compositions of the invention are not administered by invasive modes of treatment (i.e., are non-invasive). In certain embodiments, the metadoxine compositions are not administered by intravenous injection.

In certain embodiments, compositions of the invention are delivered as a microcrystalline powder or a solution suitable for nebulization; for intravaginal or intrarectal administration, pessaries, suppositories, creams or foams. A preferred formulation is a formulation for oral administration. Another preferred formulation is for topical administration. Another preferred formulation is for transmucosal administration, sublingual, buccal (absorbed through cheek near gumline) administration, administration by inhalation or ocular administration, e.g., in eye drops.

Administration of metadoxine for medical uses requires safe and efficient delivery systems. The present invention provides delivery systems for safe delivery of a variety of substances due to their special physico-chemical features, particularly direct absorption, by non-invasive means, and consequent avoidance of side effects. The delivery systems significantly enhance efficiency and quality of metadoxine absorption based on its unique physicochemical features, which enables lower concentrations or amounts of active substance to be delivered to a subject in a biologically active form. The delivery systems of the invention provide for the direct access of the active substance to the tissues and thus provide immediate or near-immediate effects of metadoxine to the subject in need thereof.

Accordingly, in certain embodiments, the present invention provides a non-invasive pharmaceutical delivery system for the improved administration of a physiologically active pyridoxine, particularly pyridoxol L,2-pyrrolidon-5 carboxylate (metadoxine), or a physiologically acceptable derivative thereof, comprising as the active ingredient said physiologically active pyridoxine in a suitable carrier for fast restoration of sobriety following alcohol consumption in a subject in need thereof, particularly wherein the subject has not reached intoxication. In certain embodiments, serum levels of the active ingredient are achieved within from about 10 to about 40-60 minutes following administration.

In another embodiment, the invention provides a non-invasive pharmaceutical delivery system for the improved administration of a physiologically active pyridoxine derivative, particularly pyridoxol L,2-pyrrolidon-5 carboxylate (metadoxine), for use in preventing or treating chronic and/or acute alcohol intoxication in a subject in need thereof, comprising as the active ingredient said pyridoxine derivative, in a suitable carrier. In certain embodiments, serum levels of said active ingredient are achieved within from about 10 to about 40-60 minutes following administration.

In certain embodiments, the drug delivery systems of the invention may be designed for oral, nasal, ocular, rectal, subcutaneous, transdermal, transmucosal, sublingual, buccal or inhalation administration. The drug delivery systems may provide the active substance in a controlled release mode. In certain embodiments, the drug delivery systems of the invention may further comprise at least one additional pharmaceutically active agent.

The delivery systems of the invention may generally comprise a buffering agent, an agent which adjusts the osmolarity thereof, and optionally, one or more pharmaceutically acceptable carriers, excipients and/or additives as known in the art. Supplementary pharmaceutically acceptable active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated. It is contemplated that the active agent can be delivered by any pharmaceutically acceptable route and in any pharmaceutically acceptable dosage form.

Oral forms include, but are not limited to, tablets, capsules, pills, sachets, lozenges, drops, powders, granules, elixirs, tinctures, suspensions, syrups, and emulsions. Also included are oral rapid-release, time controlled-release, and delayed-release pharmaceutical dosage forms. The active drug components can be administered in a mixture with suitable pharmaceutical diluents, excipients or carriers (collectively referred to herein as "carrier"), materials suitably selected with respect to the intended form of administration.

Where the delivery system is for oral administration and is in the form of a tablet or capsule or the like, the active drug components can be combined with a non-toxic pharmaceutically acceptable inert carrier such as lactose, starch, sucrose, glucose, modified sugars, modified starches, methylcellulose and its derivatives, dicalcium phosphate, calcium sulfate, mannitol, sorbitol, and other reducing and non-reducing sugars, magnesium stearate, stearic acid, sodium stearyl fumarate, glyceryl behenate, calcium stearate and the like. For oral administration in liquid form, the active drug components can be combined with non-toxic pharmaceutically acceptable inert carriers such as ethanol, glycerol, water and the like. When desired or required, suitable binders, lubricants, disintegrating agents and coloring and flavoring agents can also be incorporated into the mixture. Stabilizing agents such as antioxidants, propyl gallate, sodium ascorbate, citric acid, calcium metabisulphite, hydroquinone, and 7-hydroxycoumarin can also be added to stabilize the dosage forms. Other suitable compounds can include gelatin, sweeteners, natural and synthetic gums such as acacia, tragacanth, or alginates, carboxymethylcellulose, polyethylene, glycol, waxes and the like.

Additional suitable pharmaceutically acceptable carriers that may be used in these pharmaceutical compositions include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. In some embodiments, the pharmaceutically acceptable carrier is magnesium stearate. Additional pharmaceutical excipients commonly accepted and used are found in, for example, Remington's Pharmaceutical Sciences (Gennaro, A., ed., Mack Pub., 1990).

For purposes of parenteral administration, solutions in suitable oil such as sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art. Methods of preparing various pharmaceutical compositions with a certain amount of active ingredient are known, or will be apparent in light of this disclosure, to those skilled in this art.

The half-life of metadoxine in human serum is very short. Lu Yuan et al. (*Chin. Med. J.* 2007 120(2) 160-168) shows a mean half life of about 0.8 hour. A way of prolonging serum levels of active moiety is by administering the material in a sustained-release formulation. Because metadoxine is freely soluble in water and in various biological fluids (see Example 1), it is difficult to sustain its release and prolong its absorption time. Therefore, it was unexpected that sustained release could be achieved. A control release dosage form of metadoxine may be based on a predetermined gradual release of the active ingredient in the biological fluids, resulting in a sustained action with small fluctuations of the plasma level over a prolonged period of time.

In certain embodiments, the delivery system of this invention may be administered in controlled release formulations. In certain embodiments, the method of administration will be determined by the attending physician or other person skilled in the art after an evaluation of the subject's condition and requirements. An embodiment of the method of the present invention is to administer the therapeutic compound described herein in a sustained release form. Any controlled or sustained release method known to those of ordinary skill in the art may be used with the compositions and methods of the invention such as those described in Langer, *Science* 249(4976):1527-33 (1990). Such method comprises administering a sustained-release composition, a suppository, or a coated implantable medical device so that a therapeutically effective dose of the composition of the invention is continuously delivered to a subject of such a method. Sustained release may also be achieved using a patch designed and formulated for the purpose. The composition of the invention may be delivered via a capsule which allows sustained-release of the agent over a period of time. Controlled or sustained-release compositions include formulation in lipophilic depots (e.g., fatty acids, waxes, oils). Also comprehended by the invention are particulate compositions coated with polymers (e.g., poloxamers or poloxamines). Sustained release formulae or devices, or any topical formulations, may additionally contain compositions to stabilize the composition or permeate physiological barrier such as skin or mucous membrane. Exemplary additional components may include any physiologically acceptable detergent, or solvent such as, for example, dimethylsulfoxide (DMSO).

In certain embodiments, the metadoxine in compositions of the invention may be formulated for sustained or controlled release over a period of at least 0.5, 1, 2, 3, 4, 5, 6, 7, 8, 9, 10, 11 or 12 hours. In certain embodiments, the metadoxine in compositions of the invention may be formulated for sustained or controlled release over a period of about 0.5, 1, 2, 3, 4, 5, 6, 7, 8, 9, 10, 11 or 12 hours. In certain embodiments, the metadoxine in compositions of the invention may be formulated for sustained or controlled release over a period of between about 0.5 or 1 or 2 or 3 or 4 hours and about 5, 6, 7, 8, 9, 10, 11 or 12 hours. In certain embodiments, the metadoxine in compositions of the invention may be formulated for sustained or controlled release over a period of between about 5 or 6 or 7 or 8 hours and about 9, 10, 11 or 12 hours.

In certain embodiments, the metadoxine in compositions of the invention may be in immediate, fast of burst release form.

In certain embodiments, the metadoxine in compositions of the invention may be formulated to release up to 5, 10, 15, 20, 25, 30, 35, 40, 45, 50, 55, 60, 65, 70, 75, 80, 85, 90, 95, 99, 99.5 or 100% of the total metadoxine in about 0.5, 1, 2, 3, 4, 5, 6, 7 or 8 hours. In certain embodiments, the metadoxine in compositions of the invention may be formulated to release not less than 5, 10, 15, 20, 25, 30, 35, 40, 45, 50, 55, 60, 65, 70, 75, 80, 85, 90, 95, 99, 99.5 or 100% of the total metadoxine in about 0.5, 1, 2, 3, 4, 5, 6, 7 or 8 hours.

In certain embodiments, the metadoxine in compositions of the invention may be in a combination of sustained or slow release and immediate or fast release forms. In certain embodiments, the relative proportion of sustained or slow release metadoxine to immediate or fast release metadoxine is, e.g., 1 to 99, 5 to 95, 10 to 90, 15 to 85, 20 to 80, 25 to 75, 30 to 70, 35 to 65, 40 to 60, 45 to 55, 50 to 50, 55 to 45, 60 to 40, 65 to 35, 70 to 30, 75 to 25, 80 to 20, 85 to 15, 90 to 10, 95 to 5, or 99 to 1.

In certain embodiments, a polymeric material is used to sustain or control release of metadoxine. In certain embodiments, the type of polymeric material and the amount of which is used, have a strong influence on the rate of release of metadoxine from the product of the present invention. Examples of polymers include both hydrophobic and hydrophilic polymers. Examples of hydrophobic polymers include, but are not limited to, ethyl cellulose and other cellulose derivatives, fats such as glycerol palmito-stereate, beeswax, glycowax, castorwax, camaubawax, glycerol monostereate or stearyl alcohol, hydrophobic polyacrylamide derivatives and hydrophobic methacrylic acid derivatives, as well as mixtures of these polymers. Hydrophilic polymers include, but are not limited to, hydrophilic cellulose derivatives such as methyl cellulose, hydroxypropylmethyl cellulose, hydroxyethylcellulose, hydroxypropyl cellulose, carboxymethyl cellulose, sodium carboxymethylcellulose and hydroxyethyl methylcellulose polyvinyl alcohol, polyethylene, polypropylene, polystyrene, polyacrylamide, ethylene vinyl acetate copolymer, polyacrylate, polyurethane, polyvinylpyrrolidone, polymethylmethacrylate, polyvinyl acetate, polyhydroxyethyl methacrylate, as well as mixtures of these polymers. Furthermore, any mixture of one or more hydrophobic polymer and one or more hydrophilic polymer could optionally be used.

In certain embodiments, a polymeric material to be used in compositions of the invention is microcrystalline cellulose such as "Avicel PH 101" manufactured by FMC BioPolymer's.

In certain embodiments, a polymeric material to be used in compositions of the invention is Hydroxypropyl Methylcellulose such as "Metholose" produced by Shin-Etsu Chemical Co.

In certain embodiments, a polymeric material to be used in compositions of the invention is Ethyl cellulose such as "Ethocel™" manufactured by The Dow Chemical Company.

In certain embodiments, a polymeric material to be used in compositions of the invention is an acrylic polymer such as "Eudragit RS™" produced by Rohm GmbH.

In certain embodiments, a polymeric material to be used in compositions of the invention is a colloidal silicone dioxide such as "Aerosil™" manufactured by Degussa.

In certain embodiments, a polymeric material to be used in compositions of the invention is a Poly (Vinyl Acetate) such as "Kollicoat SR" manufactured by BASF.

In certain embodiments, a polymeric material to be used in compositions of the invention is an Ethyl Acetate and Vinyl Acetate solution such as "Duro-Tak" manufactured by Delasco Dermatologic Lab & Supply, Inc.

In certain embodiments, the composition of the invention comprises or consists essentially of Formula 1. Formula 1 comprises or consists essentially of 100-3000 mg metadoxine and 5-20,000 mg metholose.

In certain embodiments, the composition of the invention comprises or consists essentially of Formula 2. Formula 2 comprises or consists essentially of 100-3000 mg metadoxine and 5-7000 mg Ethocel E10™.

In certain embodiments, the composition of the invention comprises or consists essentially of Formula 3. Formula 3 comprises or consists essentially of 100-3000 mg metadoxine and 5-20,000 mg Eudragit RS™.

In certain embodiments, the compositions of the invention comprise or consist essentially of about 250, 300, 400, 500, 600, 700, 800, or 900 mg to about 1000, 1500, 2000, 2500 or 3000 mg metadoxine. In certain embodiments, the compositions of the invention comprise or consist essentially of about 5, 100, 500, or 1000 mg to about 2000 4000, 10,000, 15,000, or 20,000 mg Avicel PH 101™. In certain embodiments, the compositions of the invention comprise or consist essentially of about 25, 50, 100, 150, 200, 250, 300, 350, 400, 450, 500, 550 or 600 mg to about 650, 700, 750, 800, 850, 900, 950, 1000, 5000, 10,000, 15,000 or 20,000 mg of a polymeric material. In certain embodiments, the polymeric material is metholose, Ethocel E10™ or Eudragit RS™. In certain embodiments, metholose comprises or consists essentially of between 1 and 90% of the formulation, preferably between 5 and 70%. In certain embodiments, Ethocel™ comprises or consists essentially of between 1 and 30% of the formulation, preferably between 2 and 20%. In certain embodiments, Eudragit™ comprises or consists essentially of between 1 and 90% of the formulation, preferably between 5 and 70%.

In certain embodiments, delivery systems of the invention comprise delivery devices. In certain embodiments, the compositions of the invention are delivered by an osmotic process at a controlled rate such as by an osmotic pump. The system may be constructed by coating an osmotically active agent with a rate controlling semipermeable membrane. This membrane may contain an orifice of critical size through which agent is delivered. The dosage form after coming into contact with aqueous fluids, imbibes water at a rate determined by the fluid permeability of the membrane and osmotic pressure of the core formulation. This osmotic imbibitions of water result in formation of a saturated solution of active material with in the core, which is dispensed at controlled rate from the delivery orifice in the membrane.

In certain embodiments, the compositions of the invention are delivered using biodegradable microparticles. In certain embodiment, the system to prepare microparticles consists of an organic phase comprised of a volatile solvent with dissolved polymer and the material to be encapsulated, emulsified in an aqueous phase. In certain embodiments, the biodegradable polymers that can be used for the microparticle matrix, comprises polylactic acid (PLA) or the copolymer of lactic and glycolic acid (PLAGA). The PLAGA polymer degrades hydrolytically over time to its monomeric components, which are easily removed from the body through natural life processes.

The preparation may also contain an absorption enhancer and other optional components. Examples of absorption enhancers include, but are not limited to, are cyclodextrins, phospholipids, chitosan, DMSO, Tween, Brij, glycocholate, saponin, fusidate and energy based enhancing absorption equipment.

Optional components present in the dosage forms include, but are not limited to, diluents, binders, lubricants, surfactants, coloring agents, flavors, buffering agents, preservatives, stabilizing agents and the like.

Diluents, also termed "fillers" include, for example, dicalcium phosphate dihydrate, calcium sulfate, lactose, cellulose, kaolin, mannitol, sodium chloride, dry starch, hydrolyzed starches, silicon dioxide, colloidal silica, titanium oxide, alumina, talc, microcrystalline cellulose, and powdered sugar. For administration in liquid form, the diluents include, for example, ethanol, sorbitol, glycerol, water and the like.

Binders are used to impart cohesive qualities to the formulation. Suitable binder materials include, but are not limited to, starch (including corn starch and pregelatinized starch), gelatin, sugars (including sucrose, glucose, dextrose, lactose and sorbitol), polyethylene glycol, waxes, natural and synthetic gums, e.g., acacia, tragacanth, sodium alginate, celluloses, and Veegum, and synthetic polymers such as polymethacrylates and polyvinylpyrrolidone.

Lubricants are used to facilitate manufacture; examples of suitable lubricants include, for example, magnesium stearate, calcium stearate, stearic acid, glyceryl behenate, and polyethylene glycol.

Surfactants may be anionic, cationic, amphoteric or nonionic surface active agents, with anionic surfactants preferred. Suitable anionic surfactants include, but are not limited to, those containing carboxylate, sulfonate and sulfate ions, associated with cations such as sodium, potassium and ammonium ions. Particularly preferred surfactants include, but are not limited to: long alkyl chain sulfonates and alkyl aryl sulfonates such as sodium dodecylbenzene sulfonate; dialkyl sodium sulfosuccinates, such as sodium bis-(2-ethylhexyl)-sulfosuccinate; and alkyl sulfates such as sodium lauryl sulfate.

Stabilizing agents such as antioxidants, include, but are not limited to, propyl gallate, sodium ascorbate, citric acid, calcium metabisulphite, hydroquinone, and 7-hydroxycoumarin.

If desired, the present compositions may also contain minor amounts of nontoxic auxiliary substances such as wetting or emulsifying agents, preservatives, and the like.

Any of the compositions of the invention may be used alone or in combination with one or more additional therapeutic agents, for the treatment of alcohol consumption related symptoms. For examples of additional therapeutic agents see U.S. Patent Application Publication Nos. 2005/0271739, 2004/0162270 and 2002/0192303, herein incorporated by reference in their entirety.

The amount of both the compound and the additional therapeutic agent that may be combined with the carrier materials to produce a single dosage form will vary depending upon the host treated and the particular mode of administration. Preferably, the compositions of this invention should be formulated so that a dosage of between 0.1-1 g/kg body weight/day, preferably 0.1-300 mg/kg body weight, can be administered. The dose of the compound depends on the condition and the illness of the patient, and the desired daily dose. In human therapy, the oral daily dose is preferably 10-3000 mg. These doses are administered in unit dosage forms, which may be divided into 2-3 smaller doses for each day in certain cases, especially in oral treatment.

In certain embodiments, the compositions of the present invention may act synergistically in combination with each other and may further act synergistically in the presence of an additional therapeutic agent. Therefore, the amount of compound(s) and additional therapeutic agent(s) in such compositions will be less than that required in a monotherapy utilizing only that therapeutic agent. In such compositions a dosage of between 0.1-1 g/kg bodyweight/day of the additional therapeutic agent can be administered.

Use of Metadoxine to Prepare Therapeutic Compositions

In certain embodiments, the present invention provides a use of metadoxine (or a functional, physiologically acceptable derivative of metadoxine) in the manufacture of a therapeutic composition useful for administering to a subject in need thereof according to any one of the methods of the invention as described herein. In certain embodiments, the present invention provides a use of metadoxine (or a functional, physiologically acceptable derivative of metadoxine) in the manufacture of a therapeutic composition useful for administering to a subject in need thereof according to any one of the compositions of the invention as described herein.

Kits and Delivery Devices

The present invention also provides delivery devices and kits comprising a metadoxine composition of the invention, and methods for their use. Delivery devices and kits of the invention may be used for practicing each of the methods of the invention as described herein, e.g., for reducing or preventing symptoms or effects of alcohol consumption; for preventing alcohol intoxication; for reducing or eliminating blood alcohol levels in a subject, or for increasing the mean $t_{max}$ of metadoxine in the blood of a subject, among others.

In certain embodiments of this invention, kits and delivery devices of this invention may be included in a container, package or dispenser alone or as part of a kit with labels and instructions for administration. In certain embodiments of this invention, components for performing methods of this invention may be included in a container, package or dispenser alone or as part of a kit with labels and instructions for administration. In certain embodiments, the components may include means for measuring or monitoring BAC levels before, during or after administration of a metadoxine composition. Measuring or monitoring BAC levels is performed by conventional means known to one of ordinary skill in the art.

Delivery devices for use with the compositions and methods of the invention may include any devices for drug delivery known to one of ordinary skill in the art. In certain embodiments, delivery devices are used to maintain sustained or controlled release of the compositions of the invention.

EXAMPLES

The following examples are intended to be illustrative of the disclosed invention. The examples are non-limiting, and the skilled artisan will recognize that other embodiments are within the scope of the present invention. Where not otherwise noted, methods were performed using techniques that would be understood by one of ordinary skill in the art.

Example 1

Solubility Testing of Metadoxine 200 mg of metadoxine powder were weighted into 4 test tubes. For each test tube 2 g of one aqueous medium was added. Media tested were Dulbecco's PBS pH 7.2, simulated gastric fluid without pepsin USP (SGF pH 1.2), phosphate buffer 10 mM pH 4.5 and simulated intestinal fluid without pancreatin USP (SIF pH 6.8). The material was fully dissolved in all four aqueous media. Additional amount of metadoxine powder was added in 200 mg portions until maximal weight of 1.4 g was achieved.
Results:
Metadoxine (1.4 g) was dissolved in 2 g of each medium. The final concentration (w/w) was 70%.
Conclusion:
Metadoxine is freely soluble in various biological fluids.

Example 2

Immediate Release Tablets of Metadoxine 500 mg tablets were prepared using the same ingredients as the commercial product: microcrystalline cellulose and magnesium stearate.

| | |
|---|---|
| Metadoxine | 500 milligrams |
| Avicel PH 101 ™ | 100 milligrams |
| Magnesium stearate | 14 milligrams |

Materials were mixed together and compressed into tablets. Dissolution was tested using USP apparatus 2 (paddles), 50 rpm, 500 ml intestinal fluid pH=6.8, 37° C. Tablets dissolved immediately reaching 100% after 30 minutes (see FIG. 1).

Example 3

Slow Release Tablets of Metadoxine 500 mg tablets were prepared using same ingredients as the commercial product plus matrix forming polymer. Polymer selection is important to achieving slow release of this highly soluble molecule. This polymer swallows in aqueous media and forms a viscous gel which releases the active material slowly.

| | |
|---|---|
| Metadoxine | 500 milligrams |
| Avicel PH 101 ™ | 72 milligrams |
| Metholose 90SH | 250 milligrams |
| Magnesium stearate | 21 milligrams |

Materials were mixed together and compressed into tablets. Dissolution was tested using USP apparatus 2 (paddles), 50 rpm, 500 ml intestinal fluid pH=6.8, 37° C. Tablets dissolved slowly reaching 74% after 6 hours (see FIG. 1).

Example 4

Slow Release Capsules of Metadoxine

Granules were prepared using high shear granulation and vacuum drying. The choice of granulation solvent is important since it has to dissolve the polymer and not the active material.

| | |
|---|---|
| Metadoxine | 250 milligrams per capsule |
| Avicel PH 101 ™ | 51.5 milligrams per capsule |
| Metholose 90SH | 125 milligrams per capsule |

Figure 2:
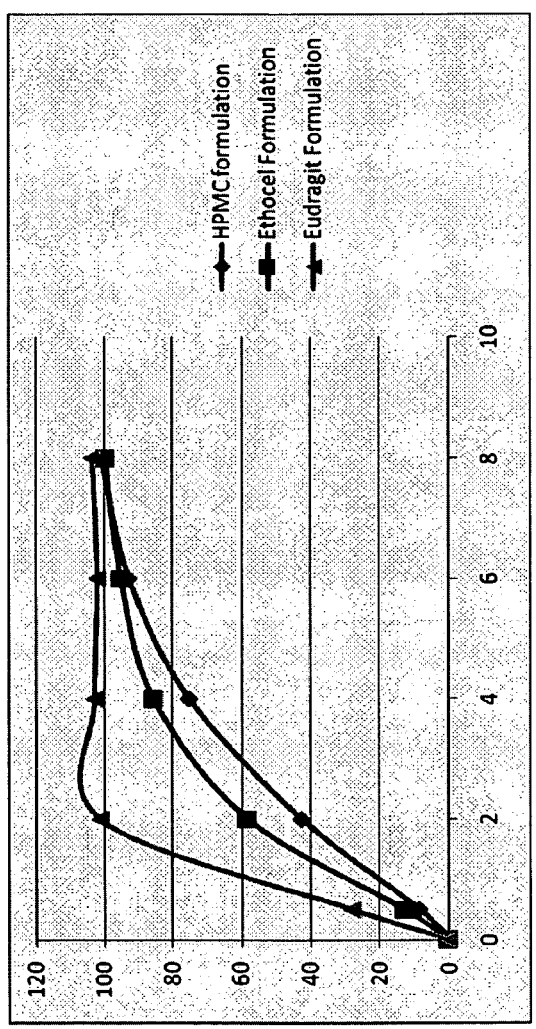
FIG. 2 illustrates exemplary dissolution rates of various slow release metadoxine formulations prepared using different polymers as describes in Examples 4-6. Metadoxine (%) released vs. time (hours).

Materials were mixed together and granulated with the aid of ethanol. Granules were filled inside gelatin capsules. Dissolution was tested using USP apparatus 2 (paddles), 50 rpm, 500 ml intestinal fluid pH=6.8, 37° C. Granules dissolved slowly reaching 75% after 4 hours (see FIG. 2).

Example 5

Slow Release Capsules of Metadoxine

Granules were prepared using high shear granulation and vacuum drying. The dissolution of this composition is by diffusion.

| | |
|---|---|
| Metadoxine | 250 milligrams per capsule |
| Avicel PH 101 ™ | 83.5 milligrams per capsule |
| Ethocel E10 ™ | 36.5 milligrams per capsule |

Materials were mixed together and granulated with the aid of ethanol. Granules were filled inside gelatin capsules. Dissolution was tested using USP apparatus 2 (paddles), 50 rpm, 500 ml intestinal fluid pH=6.8, 37° C. Granules dissolved slowly reaching 85% after 4 hours (see FIG. 2).

Example 6

Slow Release Capsules of Metadoxine

Granules were prepared using high shear granulation and vacuum drying. This is an example of an acrylic hydrophobic polymer as a polymeric material.

| | |
|---|---|
| Metadoxine | 250 milligrams per capsule |
| Avicel PH 101 ™ | 90 milligrams per capsule |
| Eudragit RS ™ | 46 milligrams per capsule |

Materials were mixed together and granulated with the solution of Eudragit RS™ solution in ethanol. Granules were filled inside gelatin capsules. Dissolution was tested using USP apparatus 2 (paddles), 50 rpm, 500 ml intestinal fluid pH=6.8, 37° C. Granules dissolved slowly reaching 100% after 2 hours (see FIG. 2).

Example 7

Controlled Release Syrup of Metadoxine

Syrup is prepared using an overhead rotary mixer.

| | |
|---|---|
| Metadoxine granules | 950 milligrams per 5 milliliters |
| Strawberry Flavor | 20 milligrams per 5 milliliters |
| Sorbitol 70% Solution | to complete volume of 5 milliliters |

Metadoxine slow release granules (from Example 5) are mixed in Sorbitol 70% solution. Strawberry Flavor is added.

Example 8

Ready to Swallow Sachets of Metadoxine

Two granulations are performed in a mixer granulator:
Granules No 1:

| | |
|---|---|
| Metadoxine | 600 milligrams |
| Cyclodextrine | 500 milligrams |

Granules No 2:

| | |
|---|---|
| Metadoxine | 800 milligrams |
| Metholose 90SH | 200 milligrams |
| Ethocel E10 ™ | 50 milligrams |

Final Mix:

| | |
|---|---|
| Magnesium Stearate | 10 milligrams |
| Aerosil 200 ™ | 10 milligrams |

Granules No 1 (enhanced absorption formula) and Granules No 2 (slow release formula) are mixed together with other ingredients and filled inside sachets.

Example 9

Metadoxine Ice Cream

Micro granules (pellets) are prepared using extrusion technology:

| | |
|---|---|
| Metadoxine | 2500 milligrams |
| Mannitol | 200 milligrams |
| Ethocel E10 ™ | 50 milligrams |

Pellets are coated in a Wurster Fluidized Bed Dryer.

| | |
|---|---|
| Kollicoat SR 30D | 200 milligrams |

Pellets are mixed with ice cream and delivered as chocolate coated ice cream cubes.

Example 10

Dermal Patch of Metadoxine

Materials (below) are mixed together to form a clear gel. The gel is coated onto a backing membrane by using coating equipment. The laminate is dried and a polyester release liner is laminated onto the dried metadoxine gel. The sheet is cut into patches and stored in a cool place.

| | |
|---|---|
| Metadoxine | 2300 milligrams |
| Durotak 387-2287 | 200 milligrams |
| Ethanol | 10 milliliters |
| Water | 5 milliliters |

Example 11

Metadoxine Chocolate Bar

Micro granules (pellets) are prepared using extrusion technology:

| | |
|---|---|
| Metadoxine | 2000 milligrams |
| Ethocel E10 ™ | 70 milligrams |

Pellets are mixed with

| | |
|---|---|
| Metadoxine | 1000 milligrams |

The mixture is incorporated inside melt chocolate bar.

Example 12

Metadoxine Effervescent Candy

Micro granules (pellets) are prepared using extrusion technology:

| | |
|---|---|
| Metadoxine | 70 milligrams |
| Metholose 90SH | 35 milligrams |

Pellets are mixed with

| | |
|---|---|
| Metadoxine | 60 milligrams |

Sodium bicarbonate 60 milligrams

| | |
|---|---|
| Citric acid | 100 milligrams |
| Sucralose | 20 milligrams |
| Cherry flavor | 10 milligrams |

The mixture is filled inside Sachets.

Example 13

Pharmacokinetic Study in Pigs

A three-way crossover bioavailability test after a single oral administration to three fasting healthy pigs was performed. One arm of the study involves 250 mg immediate release capsules—as a study control (same as current marketed formulation). The second arm of the study involves 250 mg slow-release capsules—test formulation. The third arm of the study involves intake of two 250 mg slow-release capsules (500 mg)—test formulation. The aim of this arm was to establish the optimal dose for the slow-release delivery. Usually, slow-release formulations contain higher dose than immediate release formulations and are given less frequently.

A total of 3 commercial pigs, 15-18 kg body-weight were treated. The pigs fasted 36 hours before the experiment excluding liquid food 24 hours before the experiment. The animals received the drugs orally according to the treatment arms. 3 ml of Blood were drawn into EDTA tubes before treatment and at 20', 40' 1 hr, 2 hr, 4 hr, 8 hr and 24 hr after drug administration. Blood was centrifuged, serum collected and frozen. Serum was analyzed for metadoxine content using a sensitive specific HPLC method.

Figure 3:
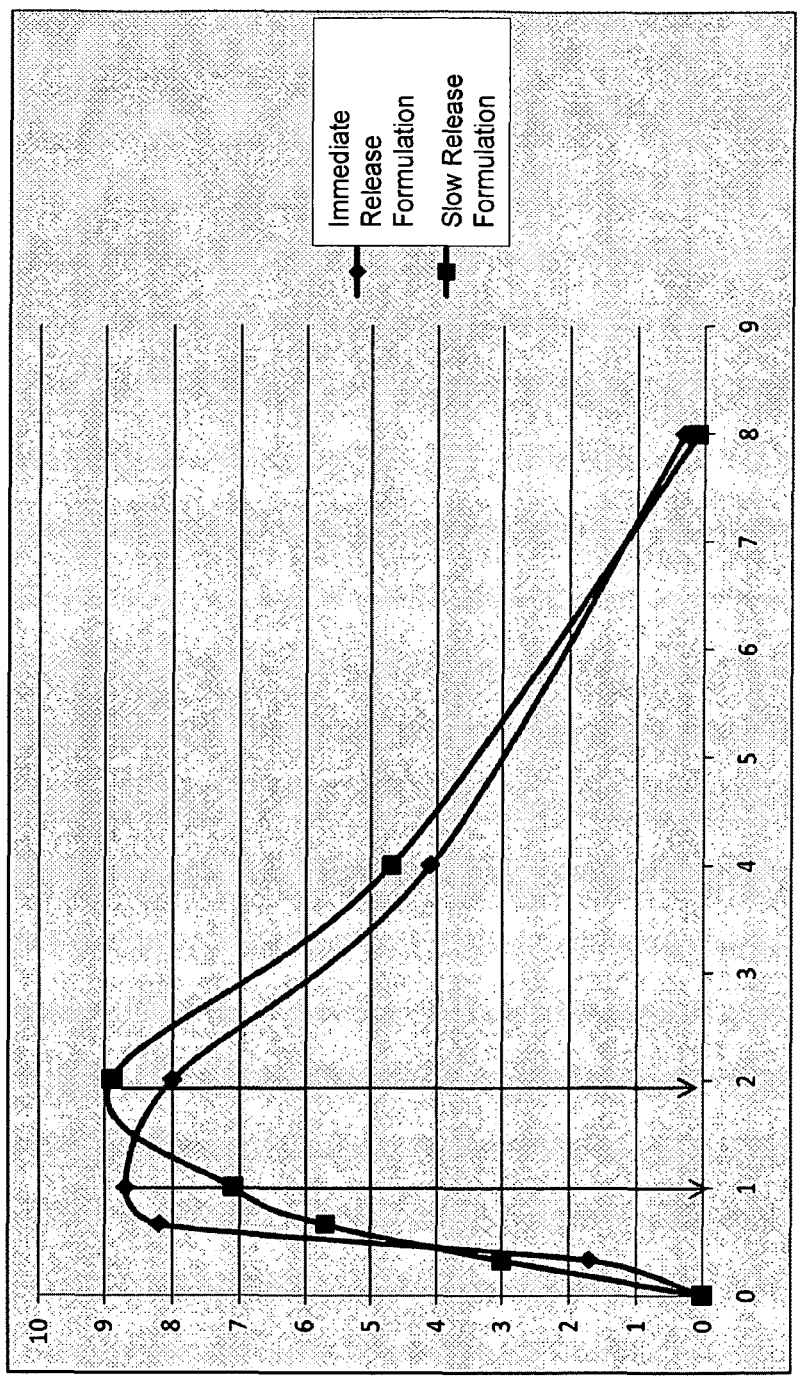
FIG. 3 illustrates metadoxine mean serum levels in 3 pigs after administration of immediate release and slow release formulations as described in Example 13. Metadoxine mean serum levels (micrograms (mcg)/ml) vs. time (hours).
Figure 4:
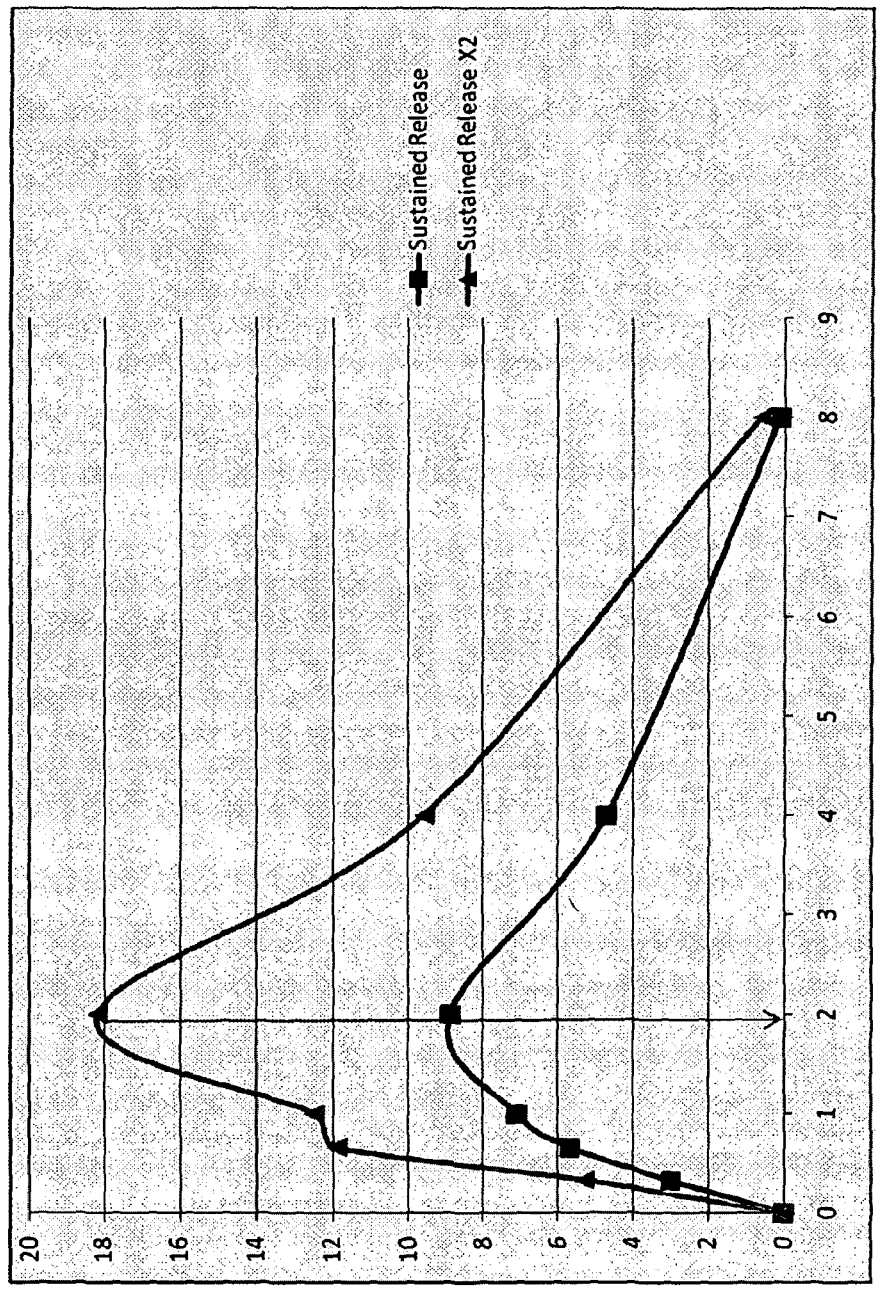
FIG. 4 illustrates metadoxine mean serum levels in 3 pigs after administration of a slow release metadoxine formulation (250 mg) and double dose (500 mg) slow release metadoxine formulations as described in Example 13. Metadoxine mean serum levels (mcg/ml) vs. time (hours).

The results show that time to peak ($t_{max}$) of the slow-release formulation is delayed (about 2 hours compared to about 1 hour of the immediate release formulation) (FIG. 3; Table 1). Area under the curve (AUC) of both formulations are similar (Table 1). When a double dose was given the $t_{max}$ is delayed to the same extent as the slow-release single dose, however, AUC was doubled (FIG. 4; Table 1).

TABLE 1

| Formulation | AUC (μg/h * ml) | Cmax (μg/ml) | Tmax (h) |
|---|---|---|---|
| Immediate release | 32.8 | 8.7 | 1 |
| Slow release | 34.9 | 8.9 | 2 |
| Slow release x2 | 69.0 | 18.2 | 2 |

Example 14

Pharmacokinetic Study in Human Subjects

A randomized three-way crossover comparative bioavailability study, with healthy fasting subjects receiving single doses of metadoxine formulations on three occasions separated by at least 3 days washout period is performed. One arm of the study involves 500 mg immediate release tablets—as a study control (same as current marketed formulation). The second arm of the study involves 500 mg slow-release tablets—test formulation. The third arm of the study involves intake of two 500 mg slow-release tablets (1000 mg)—test formulation. Blood samples are collected following a predetermined time schedule in each period in order to characterise drug absorption and elimination.

Subjects arrive in the morning, after an overnight fasting (at least 10 hours). Each subject is assigned a subject number, which is used for allocation to treatment groups. A baseline (time 0) blood specimen is obtained by aseptic venipuncture. Then each subject ingests a single dose of metadoxine, either a test or a reference product as outlined above, with 200 ml tap water. Venous blood (6 ml each) is then drawn (anticoagulated with EDTA) at 0.5, 0.75, 1, 1.5, 2, 2.5, 3, 4, 5, 6, 8, 10, 12 and 24 hours post dosing (total of 15 in each period). Each blood specimen is identified by a label specifying the study number, subject #, period and sample #. Blood samples are immediately handled and separated by centrifugation and the plasma aliquoted into 3 sets of test tubes and frozen at −75° C. (nominal) for analysis of metadoxine concentrations. Following at least a 3 day washout between periods, the procedure is repeated with each subject being dispensed an alternate product.

Human results are expected to be similar to the pigs' results of Example 13. $t_{max}$ of the slow-release formulation is delayed and AUC of both formulations are similar. When a double dose is given the $t_{max}$ is delayed to the same extent as the slow-release single dose, however, AUC is doubled.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents and patent applications are herein incorporated by reference in their entirety to the same extent as if each individual publication, patent or patent application was specifically and individually indicated to be incorporated by reference in its entirety.

The invention claimed is:

1. A method for increasing the mean $t_{max}$ of metadoxine in the blood of a subject in need thereof comprising administering a composition for oral administration comprising as the active ingredient metadoxine, wherein a portion of the metadoxine is formulated for sustained release and a portion of the metadoxine is formulated for immediate release, and wherein the relative proportion of the sustained release metadoxine portion to the immediate release metadoxine portion is in the range of from 60:40 to 80:20, in whole integers.

2. The method according to claim 1, wherein said composition has a $t_{max}$ of metadoxine in the blood that is about 2-fold greater than in an immediate release composition.

3. The method according to claim 1 or 2, wherein said composition is administered by non-chronic administration.

4. The method according to claim 3, wherein said composition is administered in a single dosage form or portion thereof.

5. The method of claim 1, wherein the total amount of the metadoxine in each portion is between about 100 and 3000 mg.

6. The method of claim 1, wherein the sustained release portion provides for release of the metadoxine for at least 8 hours.

7. The method of claim 1, wherein the total amount of the metadoxine in each portion is between 500 and 1500 mg.

8. The method of claim 1, wherein the relative proportion of the sustained release metadoxine portion to the immediate release metadoxine portion is about 65:35.

9. The method of claim 1, wherein the sustained release metadoxine portion is formulated with a combination of hydroxypropylmethyl cellulose and ethylcellulose.

10. The method of claim 1, wherein the composition further comprises at least one of a polymeric material, an absorption enhancer, and an acceptable excipient.

* * * * *